(12) United States Patent
Zarcone et al.

(10) Patent No.: US 11,766,501 B2
(45) Date of Patent: *Sep. 26, 2023

(54) MULTI-FUNCTIONAL LIGHTING FIXTURE

(71) Applicant: APOGEE LIGHTING HOLDINGS, LLC, Deer Park, NY (US)

(72) Inventors: Frank Zarcone, Smithtown, NY (US); Michael Boyd, Sayville, NY (US); Fred Katz, Hauppauge, NY (US); Richard Nicolai, St. James, NY (US)

(73) Assignee: APOGEE LIGHTING HOLDINGS, LLC, Deer Park, NY (US)

( * ) Notice: Subject to any disclaimer, the term of this patent is extended or adjusted under 35 U.S.C. 154(b) by 37 days.

This patent is subject to a terminal disclaimer.

(21) Appl. No.: 17/184,722

(22) Filed: Feb. 25, 2021

(65) Prior Publication Data

US 2021/0178008 A1    Jun. 17, 2021

Related U.S. Application Data

(63) Continuation of application No. 16/460,825, filed on Jul. 2, 2019, now Pat. No. 10,960,098.

(Continued)

(51) Int. Cl.
| | |
|---|---|
| *A61L 9/20* | (2006.01) |
| *F21V 29/67* | (2015.01) |
| *F21S 9/02* | (2006.01) |
| *F21V 23/04* | (2006.01) |
| *F21V 23/00* | (2015.01) |

(Continued)

(52) U.S. Cl.
CPC ............... *A61L 9/20* (2013.01); *A61M 21/00* (2013.01); *A61N 5/0618* (2013.01); *F21S 9/022* (2013.01); *F21V 23/003* (2013.01); *F21V 23/0435* (2013.01); *F21V 29/673* (2015.01); *H05B 47/19* (2020.01); *A61L 2202/11* (2013.01); *A61L 2209/12* (2013.01); *A61L 2209/212* (2013.01); *A61M 2021/0044* (2013.01); *F21Y 2115/10* (2016.08); *F24F 8/20* (2021.01); *F24F 8/22* (2021.01)

(58) Field of Classification Search
CPC ... F24F 13/078; F24F 1/0073; F21V 33/0088; F21S 45/30; F21S 45/33; F21S 45/37; A61L 2209/12; A61L 2/10; A61L 9/20
See application file for complete search history.

(56) References Cited

U.S. PATENT DOCUMENTS

| | | |
|---|---|---|
| 5,874,701 A | 2/1999 | Watanabe et al. |
| 6,139,803 A | 10/2000 | Watanabe et al. |

(Continued)

FOREIGN PATENT DOCUMENTS

| | | | |
|---|---|---|---|
| CN | 2464308 Y | 12/2001 | |
| JP | 10038361 A | * 2/1998 | .......... F21V 33/0088 |

(Continued)

*Primary Examiner* — Colin J Cattanach
(74) *Attorney, Agent, or Firm* — Tutunjian & Bitetto, P.C.

(57) ABSTRACT

A lighting fixture includes a first compartment including a light sealed air plenum and a first lighting source arranged in the plenum to irradiate passing air through the plenum to destroy pathogens. A second compartment is configured to be external to the first compartment. A second lighting source is arranged in the second compartment to illuminate an area adjacent to the second compartment.

19 Claims, 5 Drawing Sheets

Related U.S. Application Data (60) Provisional application No. 62/693,756, filed on Jul. 3, 2018.

(51) Int. Cl.
*A61N 5/06* (2006.01)
*A61M 21/00* (2006.01)
*H05B 47/19* (2020.01)
*F21Y 115/10* (2016.01)
*F24F 8/20* (2021.01)
*F24F 8/22* (2021.01)

(56) References Cited

U.S. PATENT DOCUMENTS

| | | | |
|---|---|---|---|
| 7,703,951 B2 | 4/2010 | Piepgras et al. | |
| 8,231,256 B1 | 7/2012 | Coleman et al. | |
| 8,362,713 B2 | 1/2013 | Recker et al. | |
| 8,829,799 B2 | 9/2014 | Recker et al. | |
| 9,358,313 B2 | 6/2016 | Deal | |
| 9,642,358 B2 | 5/2017 | Cai et al. | |
| 9,699,869 B2 | 7/2017 | Holland et al. | |
| 9,724,440 B2 | 8/2017 | Bugenske et al. | |
| 10,960,098 B2 * | 3/2021 | Zarcone | F21V 23/0435 |
| 2003/0170151 A1 * | 9/2003 | Hunter | B01J 19/123 |
| | | | 588/303 |
| 2008/0180935 A1 * | 7/2008 | Burdeen | H05B 47/19 |
| | | | 362/20 |
| 2009/0154148 A1 * | 6/2009 | Meyer | F21S 6/005 |
| | | | 315/86 |
| 2011/0001060 A1 * | 1/2011 | Welker | F24F 13/078 |
| | | | 250/455.11 |
| 2013/0291735 A1 * | 11/2013 | Livchak | F24F 13/26 |
| | | | 165/48.1 |
| 2017/0238401 A1 | 8/2017 | Sadwick et al. | |
| 2017/0276205 A1 | 9/2017 | Ogawa et al. | |
| 2018/0299117 A1 * | 10/2018 | Min | F24F 13/06 |
| 2019/0358584 A1 * | 11/2019 | Pendo | B01D 53/84 |

FOREIGN PATENT DOCUMENTS

| | | | | |
|---|---|---|---|---|
| KR | 20180057394 A | * | 5/2018 | F21V 33/0088 |
| WO | 2016099508 A1 | | 6/2016 | |
| WO | WO2019080972 A1 | * | 5/2019 | F21V 33/0088 |

\* cited by examiner

MULTI-FUNCTIONAL LIGHTING FIXTURE

TECHNICAL FIELD

The present invention is directed to germicidal light fixtures and more particularly to lamps purifying air and surfaces and including a multiplicity of features such as backup lighting for power failures and a negative ion generator.

DESCRIPTION OF THE RELATED ART

Airborne organisms can spread disease. In many indoor environments, attempts have been made to filter air passing through a ventilation system. However, in many instances improper maintenance of these filters can lead to additional problems.

SUMMARY

Embodiments of the present invention provide a configurable light, suitable for institutional usage. The light can be configured to accomplish a wide variety of lighting tasks and can be utilized to minimize the presence of pathogens in the environment where the light is located.

A lighting fixture includes a first compartment including a light sealed air plenum and a first lighting source arranged in the plenum to irradiate air passing through the plenum to destroy pathogens. A second compartment is configured to be external to the first compartment. A second lighting source is arranged in the second compartment to illuminate an area adjacent to the second compartment.

In another embodiment, the first compartment includes ultraviolet light emitting diodes. The first compartment can include light containing baffles. The air is preferably forced through the first compartment using a fan, blower or other air moving device. The first compartment may include one or more screens and/or filters. The first compartment can also include a negative ion generator. The second lighting source can include a configurable array of lights that provides color for one or more of setting a mood, providing therapy and promoting healing as well as providing room illumination. A backup battery and a backup light can be provided for use in power outages. A radio frequency identification chip can be mounted on the fixture to permit remote identification of the fixture. The fixture can be configured to fit into a standard light bay. The fixture can be controlled remotely either through wiring, an infrared data link or through a wireless link.

BRIEF DESCRIPTION OF THE DRAWINGS

The disclosure will provide details in the following description of preferred embodiments with reference to the following figures wherein.

DETAILED DESCRIPTION

In accordance with embodiments of the present invention, a configurable, multipurpose lighting fixture is provided. The lighting fixture or lamp can include two or more separate lighting sections. Each section has a group of solid-state, light emitting diode (LED) emitters. While LED lighting is described, other lighting types may be employed, e.g., bulbs or combinations of lighting type, e.g., bulbs and LEDs. An external lighting section or sections is/are utilized for normal room illumination. In addition, an internal section or chamber includes an emitter group employed to eliminate airborne pathogens. The embodiments described here can include configurable features, such as, backup lighting, negative ion generation, circadian lighting, color temperature lighting, air filtration, odor elimination and modular feature configuration. The present embodiments are suitable for use in hospitals, physician's suites, transportation stations, homes, business offices, etc. In one embodiment, a light fixture is configurable during manufacture or in operation to include or eliminate different capabilities as will be described.

In particularly useful embodiments, the lighting fixture can be employed where air treatment is needed locally. For example, in a hospital environment, HVAC circulation is not desirable between rooms or wards as airborne pathogens can be spread. By providing light fixtures that circulate air within a room, that can purify the air at the same time and that can heat or cool the air, patients are better protected and better cared for. In addition, the light fixture can be employed to assist in treatment of the patients, by adjustment of mood and to provide calming effects.

The present embodiments can include configurable light sources, e.g., for circadian rhythm illumination, for a full range of color presentation, for a full spectrum sunlight illumination with color temperature modification for chroma-therapy configurable for treatment of skin disease, wound healing, premature infant treatment, depression treatment, etc. The fixture can be used for light therapy research and development and for possible feedback to compensate for LED color shift and end of LED life detection. The fixture can include a backup power failure light ultraviolet (UV) module in a light-sealed, light baffled plenum.

The fixture can be configured to include screens, charcoal filters, large particle filters, HEPA filters, etc. A negative ion generator can also be included to further condition the air. A blower/fan or other air propeller can be employed to move air through the plenum to achieve a large reduction of airborne fungus, spores, bacteria, virus and other pathogens. Heating or cooling engines or elements can also be employed for conditioning the air.

The fixture can include an equipment bay module for power conditioning, filtering, providing a fuse or circuit breaker, AC to DC switching, providing power supplies, LED drivers, power supplies with current limiting, over-temperature and short circuit protection and a bi-directional wireless or other modality of a bi-directional communication link, etc. In some embodiments, a backup battery with a trickle charger and a backup light can be provided to permit backup or emergency lighting. A status indicator driver can be provided to illuminate the status of the device for maintenance or other purposes. A temperature sensor can be employed for operational circuit feedback for the digital controller and signal conditioner, among other things.

The lighting fixtures in accordance with the present embodiments provide the ability to configure the fixture to a particular application by permitting custom plug-in LED configuration lighting modules. The multipurpose fixture can concurrently and continuously permit pathogen removal and room illumination. The fixtures can be remotely controllable and programmable, can be ganged with similar units for control of all units concurrently and can be programmed for gradual color shift, dim and un-dim over time.

In some embodiments, the light fixture can be employed to substitute for standard lighting, such as fluorescent lights. The fixture can be configured to fit into standard light bays for drop ceilings or the like. In other embodiments, the fixtures can be mounted on the ceiling or walls at any useful position.

It will also be understood that when an element such as a layer, region, component or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Spatially relative terms, such as "beneath," "below," "lower," "above," "upper," and the like, may be used herein for ease of description to describe one element's or feature's relationship to another element(s) or feature(s) as illustrated in the FIGS. It will be understood that the spatially relative terms are intended to encompass different orientations of the device in use or operation in addition to the orientation depicted in the FIGS. For example, if the device in the FIGS. is turned over, elements described as "below" or "beneath" other elements or features would then be oriented "above" the other elements or features. Thus, the term "below" can encompass both an orientation of above and below. The device may be otherwise oriented (rotated 90 degrees or at other orientations), and the spatially relative descriptors used herein may be interpreted accordingly. In addition, it will also be understood that when a layer is referred to as being "between" two layers, it can be the only layer between the two layers, or one or more intervening layers may also be present.

It will be understood that, although the terms first, second, etc. may be used herein to describe various elements, these elements should not be limited by these terms. These terms are only used to distinguish one element from another element. Thus, a first element discussed below could be termed a second element without departing from the scope of the present concept.

Figure 1:
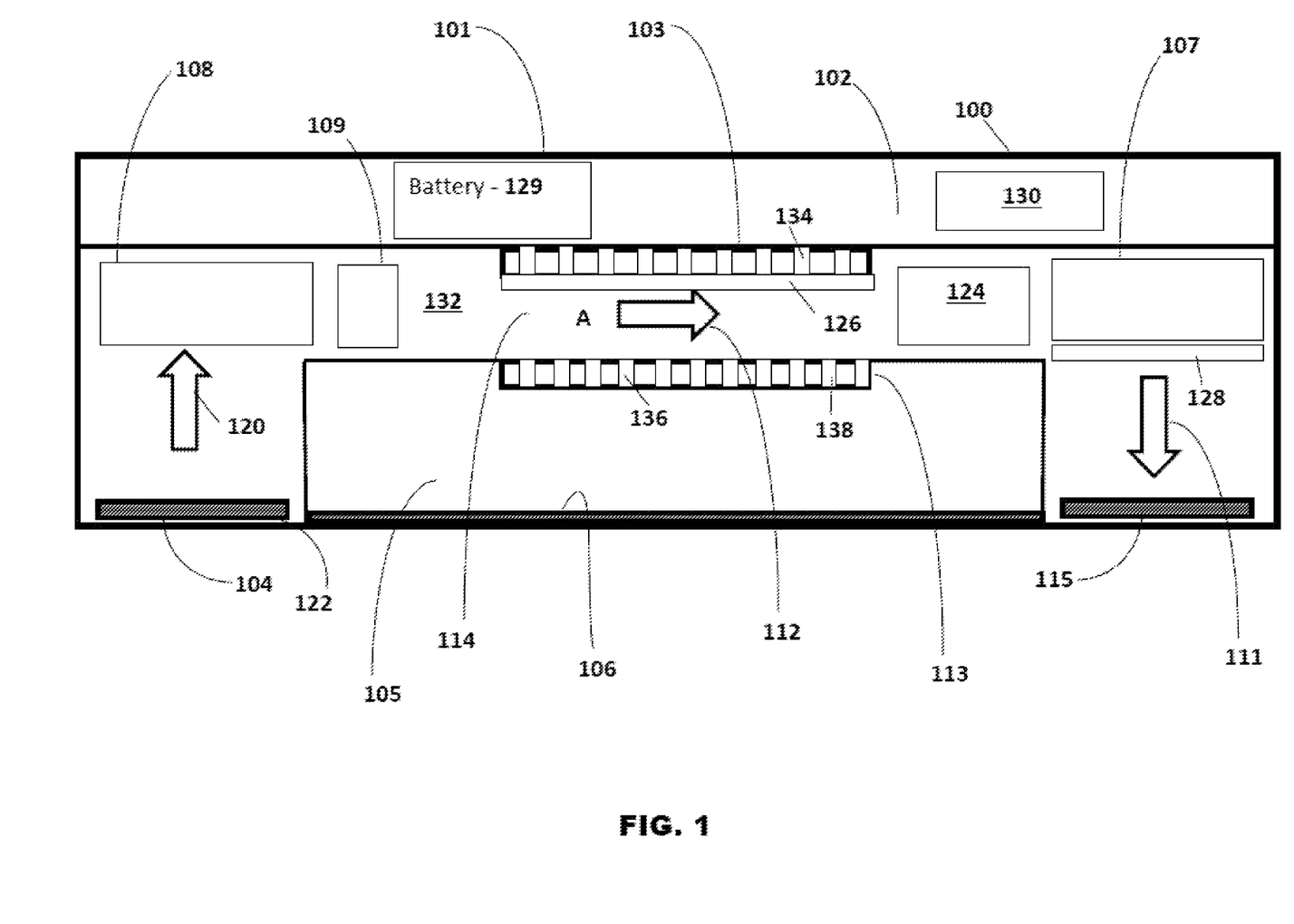
FIG. 1 is a side view of a physical construct of a light fixture that illustrates a mechanical enclosure including sheet metal construction in accordance with one embodiment.

Referring now to the drawings in which like numerals represent the same or similar elements and initially to FIG. 1, a lighting fixture 101 illustratively includes three compartments 102, 105 and 114. One compartment 102 can be for locating power supplies and other circuitry. Another compartment 114 includes a light sealed internally ultraviolet illuminated plenum that includes a convection fan or blower 108 that forces air through a light-baffled cavity or cavities. An optional charcoal odor pre-filter and/or HEPA filter 122 can be included within this construction to extract and capture dust, odor and some pathogen particles from the airflow. An optional thermoelectric or other technology cooler or heater 124 can be included to maintain the temperature of the air and/or increase the convection part of the airflow. An internal light generation source 103 can include ultraviolet (UV) bandwidths (e.g., UVC), or other color, solid state light emitters.

When air is illuminated with specific ultraviolet wavelengths, there are effects on the pathogens that exist within that air. This illumination can result in the reduction of viruses, bacteria, fungi, and mold spores within the airflow, in accordance with the illuminating wavelengths. Depending upon the wavelength of the ultraviolet lighting utilized, a quantity of ozone may be generated. This can be prevented through the use of optical filters 126 (to remove specific ozone producing wavelengths) on the light sources 103 and/or through chemical methods, e.g., providing reactive materials to reduce ozone generation. Another optional feature can include a negative ion generator 128, which can affect mood, reduce airborne smoke and ambient odors.

A room illumination compartment 105 includes lighting structures and can include sterilization features as well. In some embodiments, both the internal (e.g., within compartment 114) and external lighting (e.g., within compartment 105) structures can accept a wide array of exchangeable, individual LED lighting modules that can either be a single color such as white, that is close to sunlight balanced or a color grouped combination suitable for creation of a wide palette of colors. This color grouping can be either configured for various color temperatures of white light or built for a broad range color palette from infrared (e.g., for heating), through the visual colors and ultraviolet, or just the normally visible colors. All lighting modules utilized shall be individually addressable and capable of being both remotely programmed and controlled, switched, flashed, dimmed, sequenced and monitored using circuitry 130. The lighting modules can include different functions in each compartment 105, 114. For example, each compartment 105, 114 can have backup lighting, UV lighting (multiple wavelengths of UV can be employed), color lighting, etc. It should also be noted that multiple compartments of each type can also be employed in a same fixture. For example, several illumination compartments can be employed and several plenums with UV or other functions can be employed.

Multiple lighting fixture products for embodiments of the present invention can be logically ganged to each other, synchronized and controlled in unison. The built-in control portion (e.g., circuitry 130) can have time-keeping functions as well as storage of a lighting profile that can be executed throughout the day and night without external communication. For example, several fixtures 101 in a room can be operated together using a light switch or remote control. Other more granular controls can also be provided, e.g., separate controls for illumination, HVAC and/or air purification modes.

Some constructions can include a battery 129 and be used to provide backup or emergency illumination. There are many possible applications for this type of lighting fixture with different constructions utilized for both healthcare and illumination applications. The mood and curative effects can be provided with colored lighting in conjunction with circadian rhythms and the effects of ultraviolet light exposure upon pathogens. The external lighting portion from compartment 105 can provide for programmable, adjustable and selectable hue and intensity of the generated external lighting. The fixture or lamp 101 can be employed to pursue experimental treatments in the field of color light therapy as well as a vehicle to use for classical existing light therapies. The lamp 101 can include bidirectional wireless or other modality communications for control and status indication (e.g., in the electronics bay 102).

The lamp 101 illustratively shows one mechanical enclosure of the present invention. In the example depicted sheet metal construction can be employed in a horizontal rectangular solid housing 100. A rectangular upper chamber including compartment 102, which represents an electronics bay 102 for electronic circuitry 130, can include equipment, such as, power supplies, drivers, RF antenna circuitry for communication with remote controllers, backup batteries 129, control from the thermo circuits 124, light controls (e.g., pulsations circuits, amplitude control/dimmers, etc.), or any other electrical or electronic circuits or components (e.g., transformers, switches).

A main plenum 132 is included in the compartment 114. The main plenum 132 of compartment 114 is illuminated by a light source 103. The light source 103 can include a UV light source and, in particular, a UVC light source. The light source 103 preferably includes one or more LEDs although other light sources or bulbs can be employed.

The plenum 132 has a forced internal air circulation path 112 that flows in a direction shown by arrow "A". Air enters this plenum 132 through an intake screen 104, which filters out any heavy particulate from the atmosphere and protects the plenum 132 from foreign matter or objects. An air intake path 120 is filtered by air filter(s) 122. The air filters 122 can include a small particulate filter, a HEPA filter and/or other filters. A blower motor subassembly 108 with a fan can be employed to force air through and into the plenum 114. The air passes through a UV light baffle 109, which blocks any internal UV light from emerging from the air intake screen 104. The air circulates passed the light source 103, which can be a series of LED or other emitters of a type of ultraviolet light in the UVC wavelength. The LED emitters 134 can be arranged in any useful pattern and can employ different colors or wavelengths, preferably UVC to destroy pathogens. The air travels through an exhaust UV light baffle 107, which prevents any UV light from exiting into an exhaust path 111. The exhaust air goes out an exhaust screen 115, into a room. The baffles 109 and 107 can include louvered slats, optically non-reflective finish and/or coatings, intermittent plates or other surfaces that block, redirect or absorb light while permitting gas or airflow.

An enclosed chamber or compartment 105 is provided outside the main plenum 114, where a visible light source or sources 113, are located. This area 114 includes a room illumination chamber. The visible light source 113 can be a sub-assembly of visible light emitting LEDs 136, which can simulate a light balance of sunlight. In addition to LEDs 136, additional LEDs 138 can be employed to slightly tint the color balance of the sunlight emitting LEDs to simulate the morning, evening or other color balance of sunlight to help in maintaining an occupant's circadian rhythm. Alternate sub-assemblies can be used instead or in addition to those described that permit the light to be white or be adjusted to various colors and light intensities for mood lighting or to be used for color light therapy, as needed. The visible light shines down and passes through a light diffuser 106, which breaks up and softens the emitted light. LEDs arrays (e.g., 134, 136, 138) can be removed and replaced to provide different or enhanced modes of operation.

In an alternate embodiment where humans or pets are not permitted, the light source 113 can include UV light sources to destroy pathogens below the source 113 or as a growing lamp for plants. This can also include destroying pathogens on floor areas or in an enclosure for shoes or clothing, etc. In this embodiment, a passive infrared motion detector can be mounted on the light fixture and utilized to prevent harmful emissions when a human or pet is present.

Figure 2:
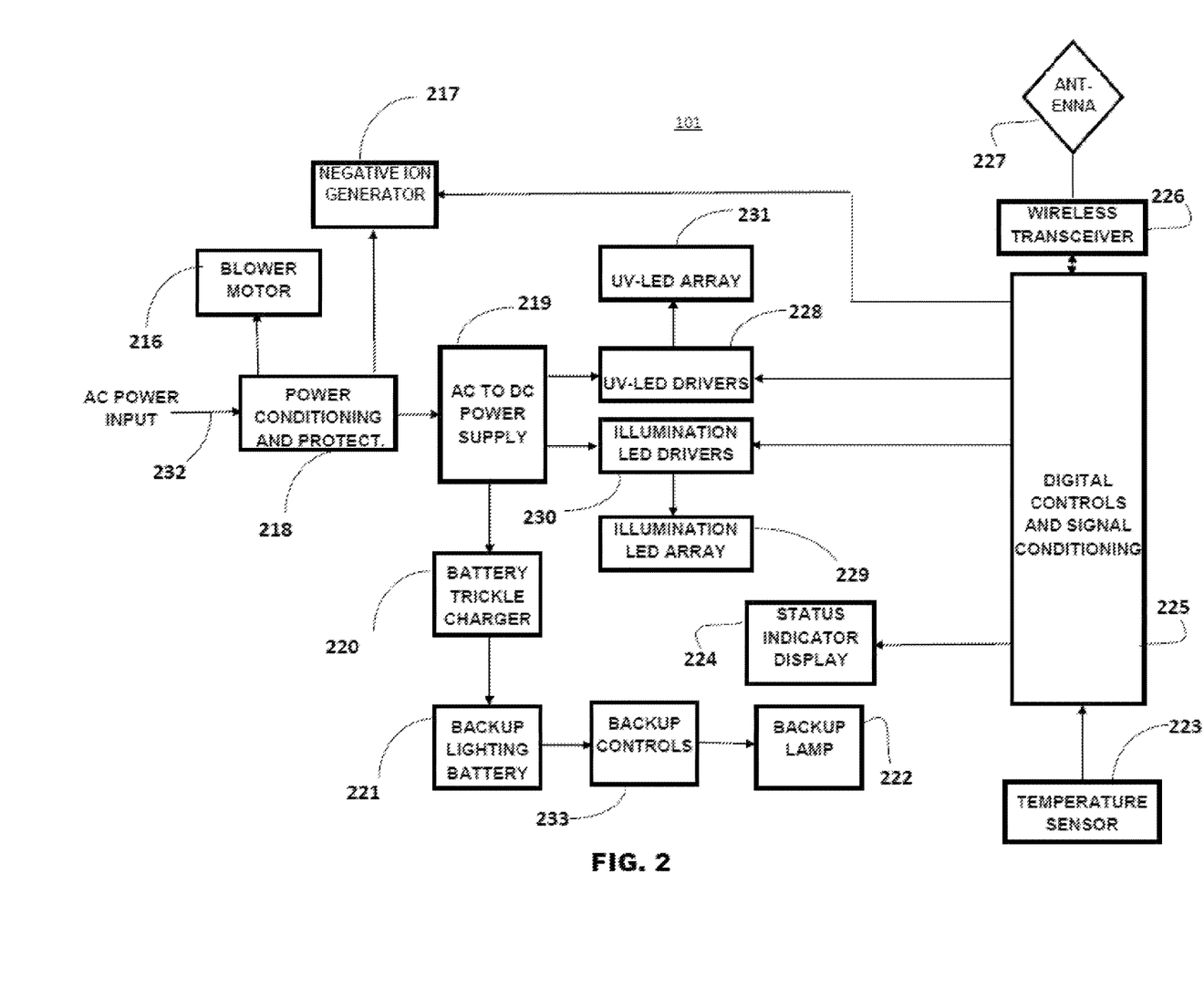
FIG. 2 is a schematic diagram showing features and capabilities of one embodiment of a light fixture in accordance with the present invention.

Referring to FIG. 2, a schematic block diagram shows electrical components in accordance with one illustrative embodiment. Some of the features/blocks are optional and can be eliminated according to a particular product or design. An alternating current (AC) power input 232 can be either standard VAC power (e.g., 115 V) or can be a higher voltage (e.g., 220 V). In some embodiments, DC power may be employed. Input power 232 can go to a power conditioning block 218 that has input power conditioning and protection. The conditioning block 218 can include capacitors, inductors and voltage spike and surge suppression components, and the protection can include a conventional fuse or fuses, a fusible resistor or a circuit breaker. The output of this block 218 goes to an AC to DC power supply 219, which can be a transformer, diode bridge, capacitor, voltage-regulator power supply or can be a switching regulator type of power supply. A blower motor/fan 216 can be powered from the conditioned AC voltage 218 or from the DC output of the AC to DC power supply 219, depending on the type of fan selected for use. The output of the power supply will feed a battery trickle charger 220, which is used to charge a backup battery 221. If power fails, a backup lamp 222 can be turned on by backup control circuitry 233. This will turn on the backup lamp or lamps 222, when the power fails. The backup lamp 222 can be placed inside the compartment 105 (or outside the compartment 105 on an external surface of the housing 100, FIG. 1).

The output of the power conditioning and protection block 218 also can be employed to power a negative ion generator 217, which is an optional piece of equipment that can remove pollen or other particulates from the air. The negative ion generator 217 is controlled by digital controls and signal conditioning circuitry 225. In addition, a temperature sensor 223 provides temperature data to the digital controls and signal conditioning circuitry 225 to alert the system if there is an over-temperature. The temperature can fluctuate, e.g., due to a circuitry failure or a blockage in the air circulation path. The digital controls and signal conditioning circuitry 225 drives a status indicator display 224, which can inform if there is a failure or a latent imminent failure, as well as mode and operational information.

LED driver modules 228 and 230 are controlled by the digital controls and signal conditioning circuitry 225. One module 228 controls LEDs (e.g., UV-LEDs) for treating air internally in the lamp fixture 101 (FIG. 1). Another module 230 is employed for controlling illumination LEDs. The module 228 drives the UV-LED array 231, while the module 230 drives the illumination LED array 229. The drivers 228, 230 are powered by the AC to DC power supply 219 and controlled by the digital controls and signal conditioning circuitry 225, which can, in one embodiment, communicate with a remote control using a wireless bi-directional channel implemented by a wireless transceiver 226 and an antenna 227. Hard wired communications or infrared links are also contemplated.

Figure 3:
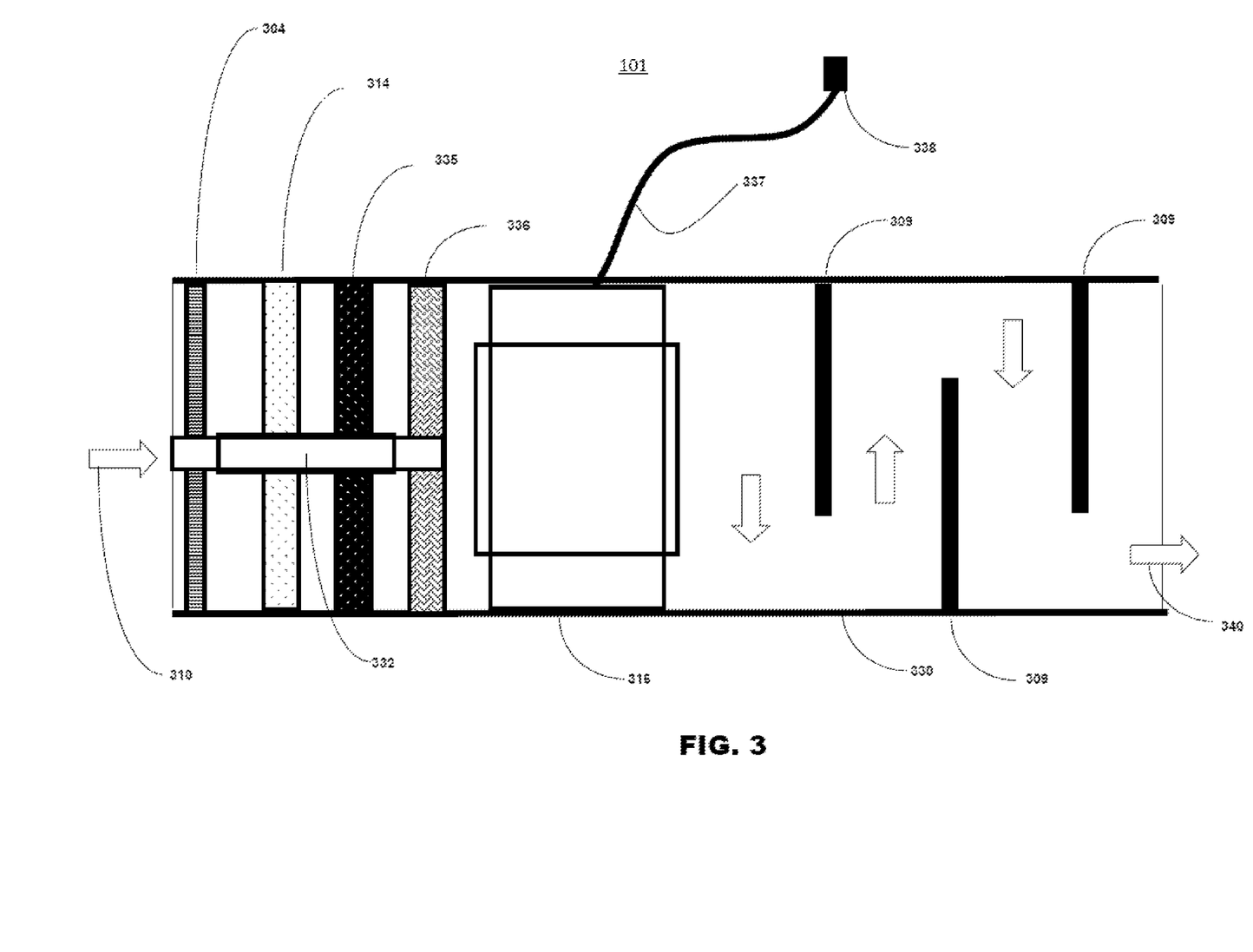
FIG. 3 is a cross-sectional view of an air intake path having screens, filters, a muffin fan (blower motor) and baffles employed to block ultraviolet C (UVC) light from inside a unit from exiting the path in accordance with one embodiment of the present invention.

Referring to FIG. 3, one embodiment shows a physical construct of an air intake path shown by arrows 310 of a lighting fixture 101. The path 310 can include screens 304, filters 314, 335, 336 a muffin fan (blower motor) 316 and baffles 309 used to block any trace of the UVC light from inside the upper unit from exiting. This path 310 could be constructed as a square cross-section sheet metal tube, with grooves to slide in the various components. In alternate embodiments, the tube can include other cross-sectional shapes, such as a circle, oval or a polygon. In addition, the sheet metal tube 330 may include an extraction handle 332, which can be employed to remove a screen/filter sub-assembly (e.g., screens 304, filters 314, 335, 336, etc.) as a quick change, scheduled service operation. Once the screen/filter sub-assembly is withdrawn, the screen/filter sub-assembly can be replaced with a cleaned module, with necessary filters replaced.

In one embodiment, the path 310 can include a coarse screen 304 used to prevent any damage to the filters and to protect the front of the unit. A fiberglass filter 314 can be employed to trap dust and some pollen particles. A charcoal filter 335 can be employed to trap odors and liquid particles. A HEPA (High-Efficiency Particulate Arresting) filter 336 can be used in medical applications or to further reduce pollen to trap 99.97% of particles that have a size greater than or equal to 0.3 microns, for example. It is preferable to put the coarser filters first in order to prevent the HEPA filter 336 36 from quickly loading up with larger particles. The HEPA filter 336 can be used to protect against airborne viral and bacterial particulates as well.

Following the HEPA filter 336 36 is the blower motor/muffin fan 316. The fan 316, depending on the particular fan selected, can be powered by AC or DC. Fan wiring 337 includes a wall plug 338 that can be used to plug in and power the entire lamp fixture unit 101.

Although the presence of the filters and fan would stop most of the ultraviolet radiation emanating from the UVC LEDs, UV light baffles 309 are provided (e.g., between 2 and 5 baffles 309), which cause the light waves to have an indirect path out. Both the light baffles 309 and an interior of the sheet metal can be coated or painted with a non-reflected material that will absorb the ultraviolet light energy and prevent the energy from exiting the air intake. In one embodiment, the baffles 309 may be fitted with UV LEDs to destroy pathogens in addition to or instead of those in the main plenum. Depending on size constraints, the baffles 309 can be located in the slide-out assembly, which can be removed using a handle similar to 332 or be located at right angles anywhere in the air exhaust path 310. During service, after a number of air intake units are replaced, the filters, screen, baffles and fan can be cleaned, off-line and be ready for the next scheduled maintenance. This would also be a good time to check the fan's bearings by inspecting the current draw of the fan.

It is to be noted that the removable sub-assembly can be constructed with individual slots that are matched to the thickness of the screen, filters and fan, for easy refurbishment during bench service after removal from the light fixture. It is also noted that the handle 332 can be included, or provisions made using holes on the front of the lamp fixture 101 to use a removable utility handle to extract the whole assembly. The exhaust air flow path 310 of the filter assembly and baffles could also include a non-removable configuration. The filters or screens employed can be varied according to the requirements of the installation site. In addition, units that have a negative ion generator may introduce the ions just past the motor 316 or in between the baffles 309.

Figure 4:
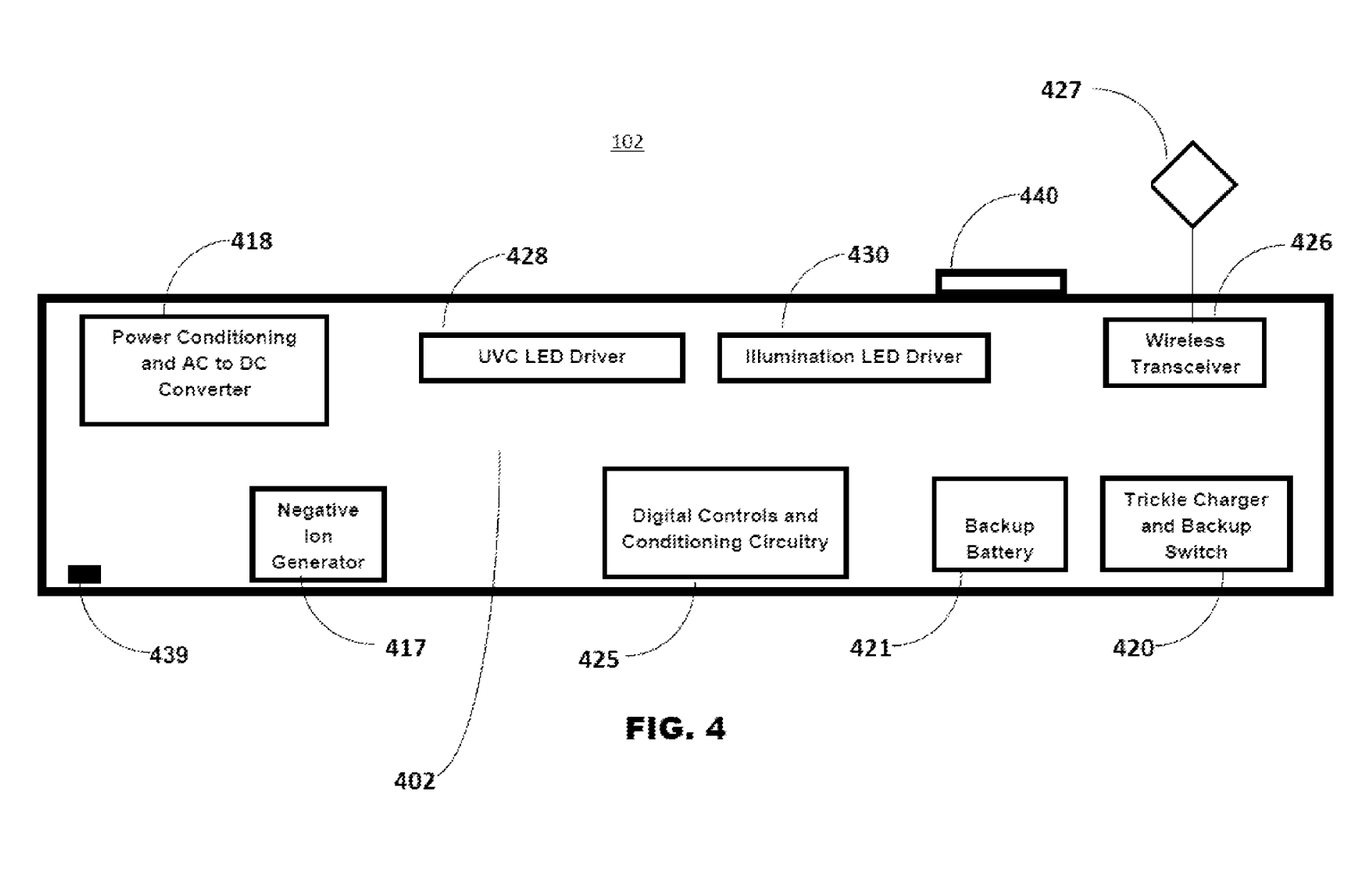
FIG. 4 is a block diagram showing an illustrative electronics bay, which is employed to locate circuitry and other features in one embodiment of a light fixture in accordance with the present invention.

Referring to FIG. 4, an electronics bay 402 (102, in FIG. 1) is schematically shown and is used to locate the circuitry and other features of a lamp fixture 101 in accordance with aspects of the present invention. A power conditioning and AC to DC converter circuit 418 is a main power processing center, which includes a fuse, fusible resistor or circuit breaker for safety protection. The digital controls and conditioning circuitry 425 includes a microcomputer, memory, a temperature sensing element, discrete outputs to control the LED drivers 428 and 430, control lines for items such as a negative ion generator 417. A backup battery 421 supplies power for an emergency/backup lamp when there is a power failure. The backup battery 421 is charged by a trickle charger and backup switch 420 20, which delivers a slow battery charge current to the battery 421. The backup switch 421 senses the power outage and turns on the emergency lamp (not shown). This emergency lamp can include a select group or subset of the visible LEDs of the plug-in illumination LED array 229 (FIG. 2).

A wireless transceiver 426 provides a bi-directional radio, or other communication modality, that is used to remotely control and monitor the operation of the lamp fixture 101. Manual control of the fixture 101 is also contemplated. An input/output signal is connected via an antenna 427. On the outside of the electronics bay is an RFID chip 440. This is a passive device that when excited by a transponder transmits a serial number or other identifier of a particular fixture 101. This permits inventory control and tracking of performance of each unit, without having to uninstall it. A fan receptacle 439 permits plugging the lamp fixture 101 into a ceiling or wall socket for power. Each of the items indicated above are preferably located in positions that will minimize wire length and maximize heat transfer.

Figure 5A:
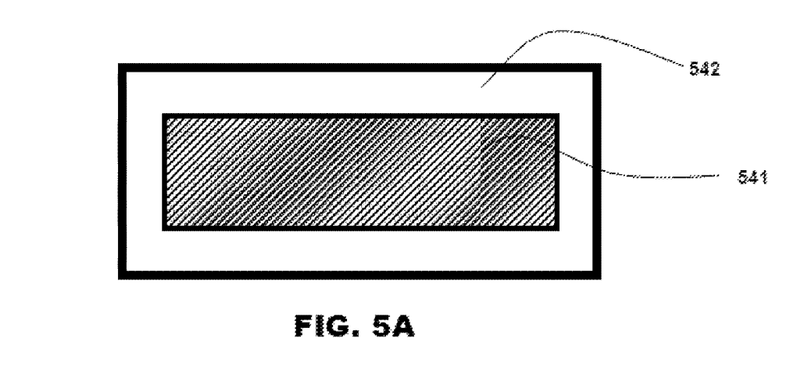
FIG. 5A shows an example of a light emitting diode (LED) plug-in array including an upper compartment which includes an ultraviolet array utilizing UVC LEDs arranged in a rectangular pattern in accordance with one embodiment.
Figure 5B:
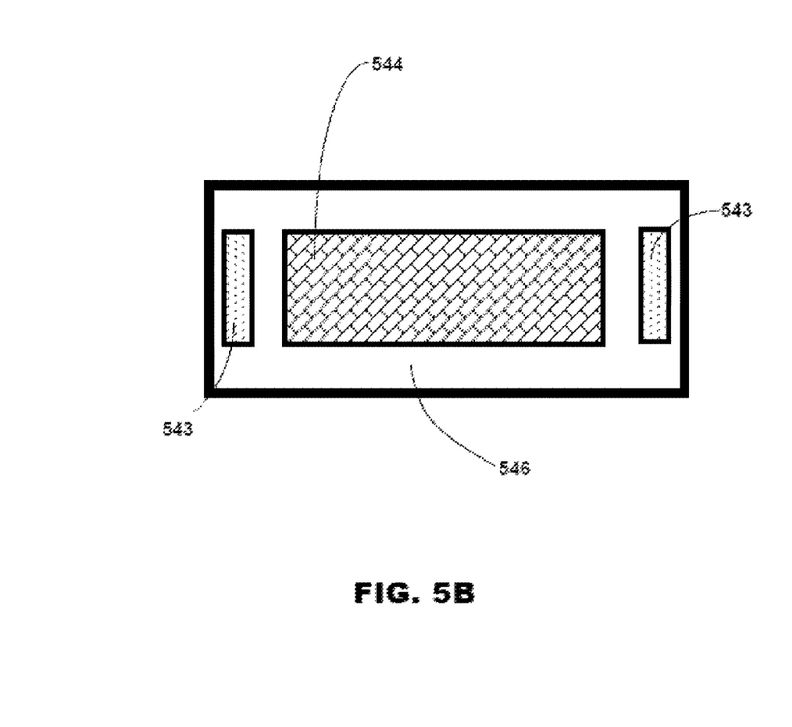
FIG. 5B shows another example of an LED plug-in array including an illumination compartment which includes a full color array and backup lighting utilizing LEDs arranged in a rectangular pattern in accordance with one embodiment.
Figure 5C:
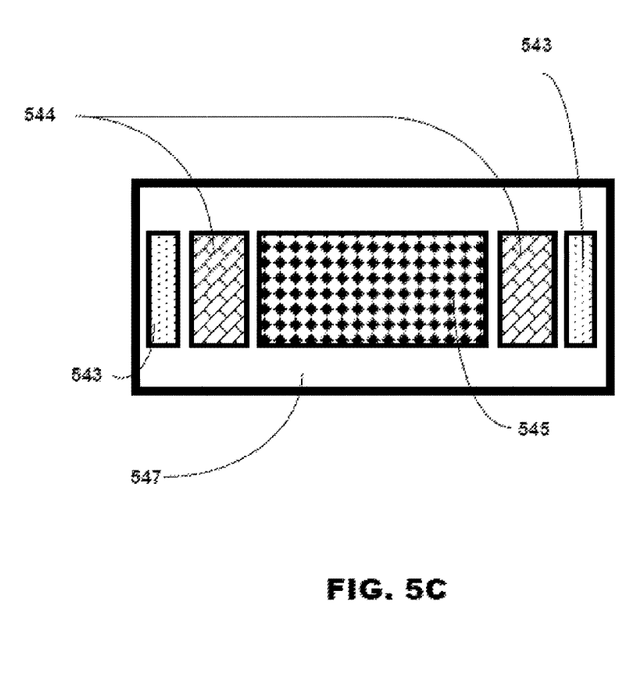
FIG. 5C shows another example of an LED plug-in array including an illumination compartment which includes a sunlight array, a color array and backup lighting utilizing LEDs arranged in a rectangular pattern in accordance with one embodiment.

Referring to FIGS. 5A-5C, examples of various LED plug-in arrays are illustratively shown in accordance with useful embodiments. FIG. 5A shows an example of an LED plug-in array 541 including an upper compartment 542 which includes an ultraviolet array utilizing UVC LEDs arranged in a rectangular pattern. FIG. 5B shows another example of an LED plug-in array including an illumination compartment 546 which includes a full color array 544 and backup lighting 543 utilizing LEDs arranged in a rectangular pattern. FIG. 5C shows another example of an LED plug-in array including an illumination compartment 547 which includes a sunlight array 545, a color array 544 and backup lighting 543 utilizing LEDs arranged in a rectangular pattern for circadian cycling. The plug-in array can be removed and replaced by a different array in accordance with the performance desired. Also, the LEDs can be configured in a plurality of different patterns and types to provide desired performance.

In one embodiment, there are two compartments in a fixture 101, one being the upper compartment which includes an ultraviolet array utilizing UVC LEDs 541 arranged in a rectangular pattern. This compartment is light sealed so that none of the ultraviolet light can exit the compartment, for human safety. This array is shown as the compartment 542 and the ultraviolet array 541. The purpose of this compartment is to irradiate the air that passes through the compartment under pressure due to a fan, and expose any pathogens to the ultraviolet radiation e.g., UVC (C wavelength of ultraviolet light), in order to kill those pathogens which may include viruses, bacteria, fungus, mold spores, pollen and other particles that promote illness. It should be understood that the UV LED array can also include backup lights (e.g., a subset of the UV array) as well in the UV range to permit continued pathogen destruction during power out situations.

The other compartment, e.g., the illumination array compartment 105 (FIG. 1), is located, e.g., directly below the upper compartment. Possible choices of lighting are shown in FIGS. 5B and 5C; however, the present invention is not limited to these, as the lighting arrangements have plug-in mounted capability such that any special purpose arrays may be substituted. The following arrays are shown as illustrative choices.

In one example in FIG. 5B, a Red/Green/Blue/Yellow, near IR, near UV LED array 544 is shown. This array can be used to generate a wide variety of colored light from the near end of infrared to the near end of ultraviolet. The uses of color lighting, both visible and invisible, can be used for therapy or patient comfort to affect a form of 'mood' lighting. On either side of the colored array can be a small backup emergency lighting LED array 543, although the backup LEDs may be arranged in any configuration and can be dispersed through array 544 or not included at all. The backup emergency lighting can be powered by a backup battery. The backup battery can be trickle charged by a battery trickle charger, which besides maintaining full charge on the battery, is used to switch the backup lighting on when power fails.

In another example, the illumination array 547 can include a circadian cycle, which projects light balanced towards natural sunlight 545 that change with time of day in color and/or intensity. In order to add circadian tint to the light, simulating different times of day from dawn until sunset, there is a second group of two smaller arrays that include Red/Green/Blue/Yellow, near infrared and near ultraviolet 544. People work better in a varying circadian lighting office, and people may do better in a healing environment with the circadian lighting variation. Although two examples are shown, there are other types of lighting configurations that can be plugged in, according to embodiments of the present invention.

Having described preferred embodiments for a multifunctional lighting fixture (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A lighting fixture, comprising:
   a first compartment including a light sealed air plenum and light containing baffles;
   a first lighting source arranged in the plenum to irradiate passing air through the plenum to destroy biological material in the air, the first lighting source including a plurality of ultraviolet (UV) light emitting diodes (LEDs) positioned directly on one or more of the light containing baffles;
   a removable sub-assembly configured for toolless removal from the lighting fixture and comprising one or more individually toollessly removable components, the components including the light containing baffles with the plurality of UV LEDs;
   a second compartment configured to be external to the first compartment; and
   a second lighting source arranged in the second compartment to illuminate an area adjacent to the second compartment.

2. The lighting fixture as recited in claim 1, wherein air is forced through the first compartment using a fan.

3. The lighting fixture as recited in claim 2, wherein the first compartment includes a negative ion generator.

4. The lighting fixture as recited in claim 1, wherein the second lighting source includes a configurable array of lights that provide color for one or more of setting a mood, providing therapy and promoting healing.

5. The lighting fixture as recited in claim 1, further comprising a backup battery and a backup light for use in power outages.

6. The lighting fixture as recited in claim 1, further comprising a radio frequency identification chip mounted on the fixture to permit remote identification of the fixture.

7. The lighting fixture as recited in claim 1, wherein the fixture fits into a standard light bay.

8. The lighting fixture as recited in claim 1, wherein the first compartment includes a filter configured to remove particulates from entering the first compartment.

9. The lighting fixture as recited in claim 1, wherein the first compartment includes a device to control temperature in a circulation path.

10. The lighting fixture as recited in claim 1, further comprising an antenna to conduct wireless communication.

11. The lighting fixture as recited in claim 1, wherein the second lighting source includes an ultraviolet source.

12. A lighting fixture, comprising:
   a housing configured for receiving a slide-out component assembly, the housing including a channel and a plurality of grooves configured for toolless receiving of the slide-out component assembly using an extraction handle, the housing forming a light sealed air plenum therethrough and comprising an air intake path including the channel, the slide-out component configured to receive one or more individually toolles sly removable components including light containing baffles with a plurality of ultraviolet (UV) light emitting diodes (LEDs);
   a first compartment including a first lighting source arranged in the plenum to irradiate passing air through the plenum to destroy biological material in the air, the first lighting source including the plurality of UV LEDs positioned directly on the light containing baffles in the first compartment;
   a second compartment configured to be external to the first compartment;
   a second lighting source arranged in the second compartment to illuminate an area adjacent to the second compartment; and
   an electronics bay mounted in the housing and including digital control circuitry to control at least one of the first lighting source and the second lighting source.

13. The lighting fixture as recited in claim 12, wherein the first compartment includes a negative ion generator and a fan.

14. The lighting fixture as recited in claim 12, wherein the second lighting source includes an individually configurable array of lights.

15. The lighting fixture as recited in claim 12, wherein the first compartment includes a device to control temperature in a circulation path.

16. The lighting fixture as recited in claim 12, wherein components of the slide-out component assembly are configured for toolless removal and receiving from the slide-out component assembly, and include at least one of a light emitting diode (LED) array, a screen, and a filter.

17. A lighting fixture, comprising:
   a first compartment including a light sealed air plenum;
   a first lighting source arranged in the plenum to irradiate passing air through the plenum, the first lighting source including a plurality of ultraviolet (UV) light emitting diodes (LEDs) positioned directly on one or more light containing baffles in the first compartment, each of the plurality of UV LEDs being individually controllable relative to each other;
   a removable sub-assembly, positionable in an air intake path of the lighting fixture, the sub-assembly being configured for toolless removal from the lighting fixture, the sub-assembly comprising one or more individually toollessly removable components, the components including light containing baffles with a plurality of individually controllable ultraviolet (UV) LEDs;
   a second compartment configured to be external to the first compartment; and
   a second lighting source arranged in the second compartment to illuminate an area adjacent to the second compartment.

18. The lighting fixture as recited in claim 17, wherein the sub-assembly comprises a plurality of grooves configured for receiving the one or more individually toollessly removable components.

19. The lighting fixture as recited in claim 18, wherein the individually toolles sly removable components include one or more of a light-emitting diode (LED) array, a screen, and a filter.

* * * * *